US012799218B2

(12) United States Patent
Zhang et al.

(10) Patent No.: US 12,799,218 B2
(45) Date of Patent: Nov. 17, 2026

(54) THERAPEUTIC DRUG FOR POLYCYTHEMIA

(71) Applicants: PERSEUS PROTEOMICS INC., Tokyo (JP); JUNTENDO EDUCATIONAL FOUNDATION, Tokyo (JP)

(72) Inventors: Lilin Zhang, Tokyo (JP); Fumiko Nomura, Tokyo (JP); Norio Komatsu, Tokyo (JP); Marito Araki, Tokyo (JP)

(73) Assignees: PERSEUS PROTEOMICS INC., Tokyo (JP); JUNTENDO EDUCATIONAL FOUNDATION, Tokyo (JP)

( * ) Notice: Subject to any disclaimer, the term of this patent is extended or adjusted under 35 U.S.C. 154(b) by 1051 days.

(21) Appl. No.: 17/640,645

(22) PCT Filed: Sep. 4, 2020

(86) PCT No.: PCT/JP2020/033561
§ 371 (c)(1),
(2) Date: Mar. 4, 2022

(87) PCT Pub. No.: WO2021/045184
PCT Pub. Date: Mar. 11, 2021

(65) Prior Publication Data

US 2023/0220098 A1 Jul. 13, 2023

(30) Foreign Application Priority Data

Sep. 4, 2019 (JP) ................................ 2019-161344

(51) Int. Cl.

| | |
|---|---|
| ***C07K 16/28*** | (2006.01) |
| ***A61K 31/17*** | (2006.01) |
| ***A61K 39/00*** | (2006.01) |
| ***A61K 45/06*** | (2006.01) |
| ***A61P 35/00*** | (2006.01) |

(52) U.S. Cl.
CPC .......... *C07K 16/2881* (2013.01); *A61K 31/17* (2013.01); *A61K 45/06* (2013.01); *A61P 35/00* (2018.01); *A61K 2039/505* (2013.01)

(58) Field of Classification Search
None
See application file for complete search history.

(56) References Cited

U.S. PATENT DOCUMENTS

| | | | | | |
|---|---|---|---|---|---|
| 2009/0010886 | A1 | 1/2009 | Zeldis | | |
| 2015/0291697 | A1* | 10/2015 | Kurosawa | A61P 35/00 | 435/254.2 |
| 2018/0134797 | A1 | 5/2018 | Zhang et al. | | |
| 2022/0332838 | A1* | 10/2022 | Zhang | A61P 43/00 | |
| 2023/0220098 | A1* | 7/2023 | Zhang | A61P 35/00 | 424/143.1 |
| 2023/0250180 | A1* | 8/2023 | Nomura | A61P 35/00 | 530/387.9 |
| 2024/0288453 | A1* | 8/2024 | Kiyoi | G01N 33/57426 | |
| 2024/0352142 | A1* | 10/2024 | Katsumi | A61P 43/00 | |

FOREIGN PATENT DOCUMENTS

| | | | | |
|---|---|---|---|---|
| CN | 104797600 | A | | 7/2015 |
| CN | 107250158 | A | | 10/2017 |
| EP | 2 918 603 | A1 | | 9/2015 |
| JP | 2007-536221 | A | | 12/2007 |
| JP | 2018-24615 | A | | 2/2018 |
| JP | 2018024615 | A | * | 2/2018 |
| JP | 2018-505652 | A | | 3/2018 |
| WO | WO2005/112917 | A1 | | 12/2005 |
| WO | WO2014/073641 | A1 | | 5/2014 |
| WO | WO2016/081640 | A1 | | 5/2016 |
| WO | WO2016/081643 | A1 | | 5/2016 |

OTHER PUBLICATIONS

Ni et al., The Protein Journal, 43, pp. 683-696, Jul. 2024 (Year: 2024).*
Parasuraman et al., Exp Hematol Oncol. (2016) 5: 3, Publication Date: Feb. 1, 2016 (Year: 2016).*
Extended European Search Report for corresponding European Application No. 20860454.6, dated Sep. 25, 2023.
Raedler, "Diagnosis and Management of Polycythemia Vera: Proceedings from a Multidisciplinary Roundtable," American Health & Drug Benefits, vol. 7, No. 7, Oct. 2014, pp. S36-S47.
Butcher et al., "Molecular aspects of polycythemia vera (Review)," International Journal of Molecular Medicine, vol. 6, 2000, pp. 243-252, 10 pages total.
Daniels et al., "The transferrin receptor part I: Biology and targeting with cytotoxic antibodies for the treatment of cancer," Clinical Immunology, vol. 121, 2006, pp. 144-158, 15 pages total.
International Preliminary Report on Patentability and Written Opinion of the International Searching Authority (Forms PCT/IB/373 and PCT/ISA/237) for International Application No. PCT/JP2020/033561, dated Mar. 8, 2022, with an English translation.
International Search Report (Forms PCT/ISA/210 and PCT/ISA/220) for International Application No. PCT/JP2020/033561, dated Nov. 2, 2020, with an English translation.
Khatun et al., "Immunohistochemical Study of Transferrin Receptor Expression in the Placenta of Pre-eclamptic Pregnancy," Placenta, vol. 24, 2003, pp. 870-876, 7 pages total.
Levy et al., "Transferrin receptor is neccessary for development of erythrocytes and the nervous system," Nature Genetics, vol. 21, 1999, pp. 396-399, 4 pages total.

(Continued)

*Primary Examiner* — Peter J Reddig
*Assistant Examiner* — Cheng Lu
(74) *Attorney, Agent, or Firm* — Birch, Stewart, Kolasch & Birch, LLP

(57) ABSTRACT

It is an object of the present invention to provide a therapeutic drug for polycythemia. According to the present invention, provided is a therapeutic drug for polycythemia, comprising an antibody which recognizes the amino acids at positions 629 to 633 of a human transferrin receptor.

11 Claims, 4 Drawing Sheets

Specification includes a Sequence Listing.

(56) References Cited

OTHER PUBLICATIONS

Ponka et al., "The transferrin receptor: role in health and disease," The International Journal of Biochemistry & Cell Biology, vol. 31, 1999, pp. 1111-1137, 27 pages total.
Richardson et al., "The molecular mechanisms of the metabolism and transport of iron in normal and neoplastic cells," Biochimica et Biophysica Acta, vol. 1331, 1997, pp. 1-40, 40 pages total.
Tefferi et al., "Survival and prognosis among 1545 patients with contemporary polycythemia vera: an international study," Leukemia, vol. 27, 2013, pp. 1874-1881, 8 pages total.
Chinese Office Action and Search Report for corresponding Chinese Application No. 202080062640.9, dated May 25, 2023, with English translation.
Japanese Office Action for Japanese Application No. 2021-544045, dated Apr. 16, 2024, with English translation.

* cited by examiner

[Fig. 1]
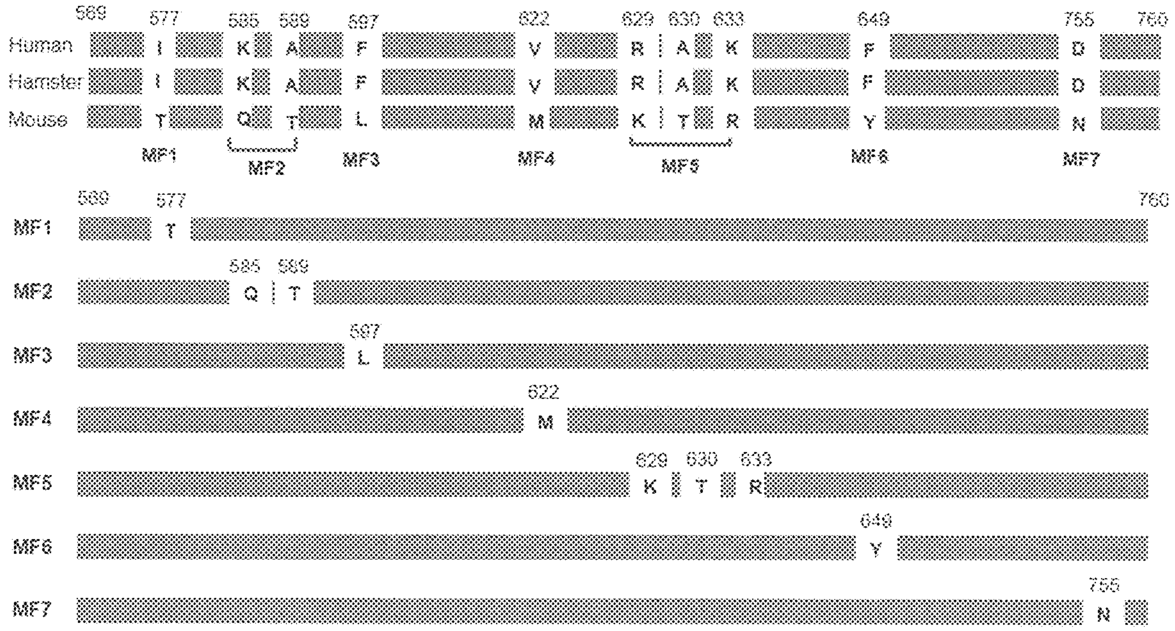

[Fig. 2]
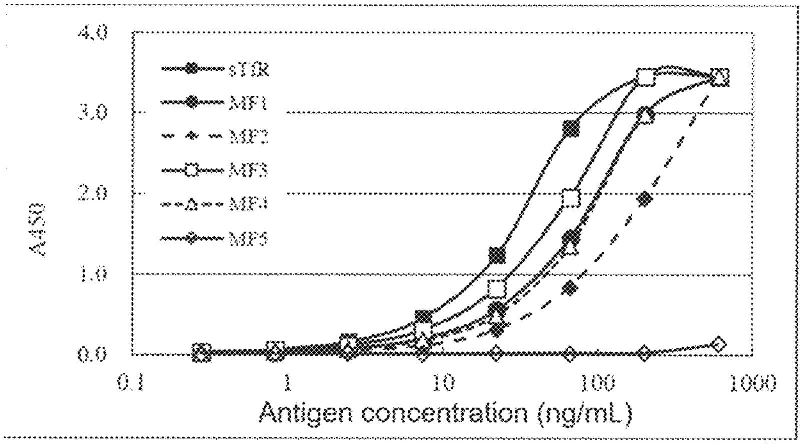
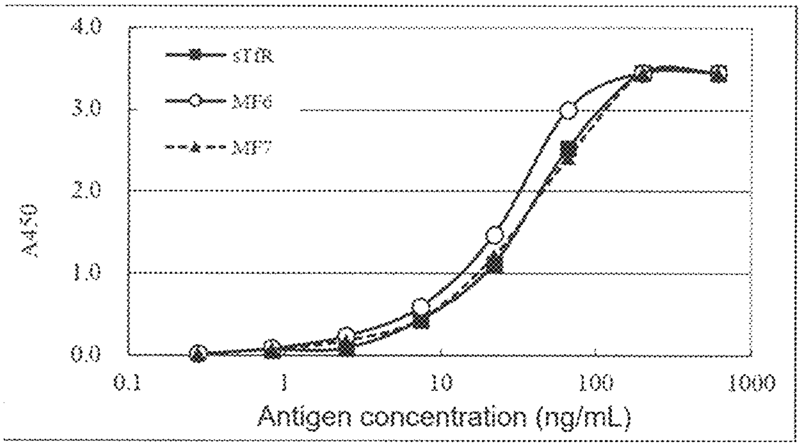

[Fig. 3]
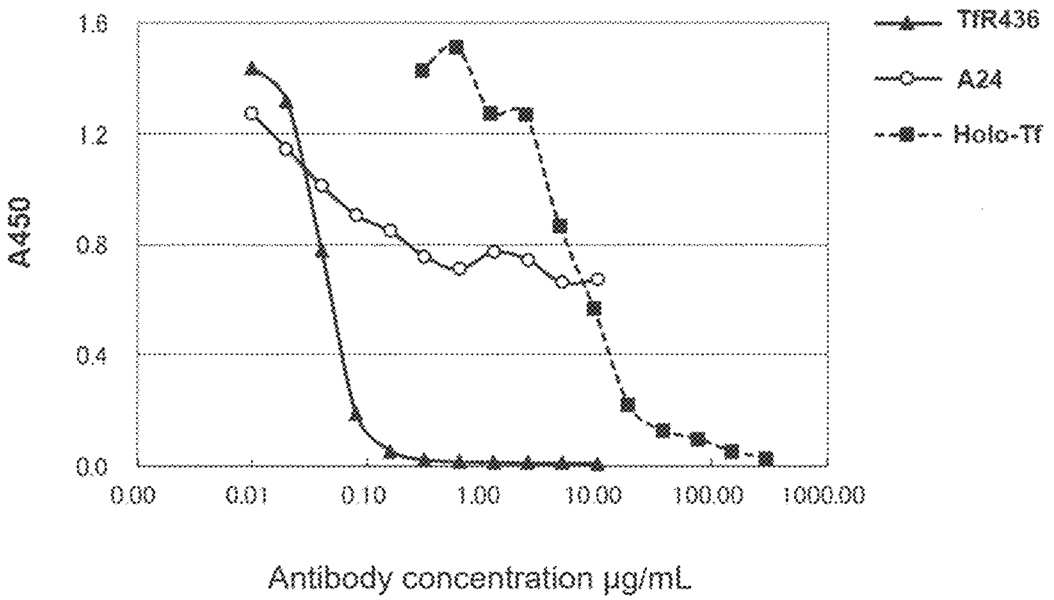
[Fig. 4]
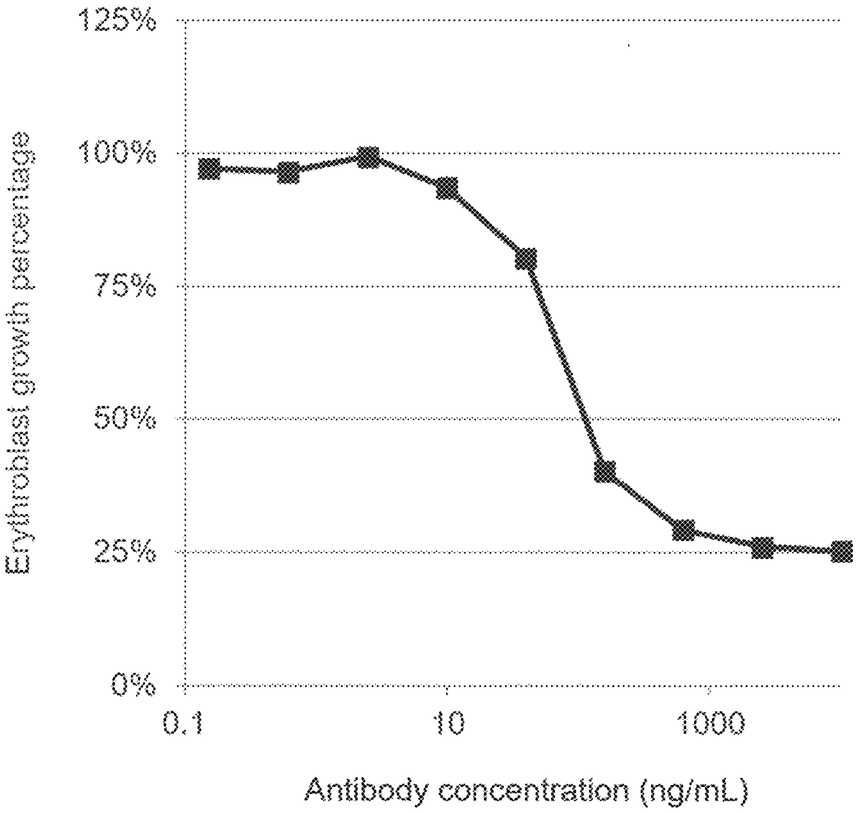

[Fig. 5]

| | | PPMX-T003 (ng/mL) | | | | |
|---|---|---|---|---|---|---|
| | | 0 | 37.5 | 75 | 150 | 300 |
| HU (μM) | 0 | 0% | (A) 23% | 48% | 69% | 75% |
| | 31.3 | 15% | 54% | 89% | 93% | 94% |
| | 62.5 | 28% | (B) 83% | 95% | 96% | 96% |
| | 125 | 52% | 94% | (C) 97% | 98% | 97% |
| | 250 | 76% | 98% | 99% | 98% | 99% |

[Fig. 6]

| | | PPMX-T003 (ng/mL) | | | | |
|---|---|---|---|---|---|---|
| | | 0 | 37.5 | 75 | 150 | 300 |
| HU (μM) | 0 | 4% | 4% | 6% | 12% | 16% |
| | 31.3 | 5% | 9% | 40% | 54% | 55% |
| | 62.5 | (A) 7% | 27% | 65% | (B) 70% | 71% |
| | 125 | 6% | 61% | 79% | 84% | 77% |
| | 250 | 17% | 80% | 87% | 85% | 89% |

THERAPEUTIC DRUG FOR POLYCYTHEMIA

This application includes an electronically submitted sequence listing in .txt format. The .txt file contains a sequence listing entitled "2022-09-06_2870-0798PUS1_ST25.txt" created on Sep. 6, 2022 and is 10,566 bytes in size. The sequence listing contained in this .txt file is part of the specification and is hereby incorporated by reference herein in its entirety

TECHNICAL FIELD

The present invention relates to a therapeutic drug for polycythemia, comprising an anti-transferrin receptor antibody.

BACKGROUND ART

Transferrin receptor (TfR) is a type II membrane protein which is expressed on the surface of a cell. TfR binds to transferrin serving as a ligand, so that it imports iron into a cell and maintains the survival and division of the cell. It has been reported that the expression level of TfR is low in a majority of normal cells, but that TfR is expressed in several types of cells such as, for example, skin epidermal basal cells and small intestinal epithelial cells (Non-Patent Documents 1 to 3). Since there is a high demand for iron uptake in erythroblast cells and placental trophoblast cells, TfR is highly expressed in these cells (Non-Patent Documents 4 and 5).

Polycythemia vera (PV) is a chronic myeloproliferative neoplasm which is characterized by an excessive increase in erythrocytes. Clinical findings of PV may include acceleration of blood viscosity due to an increase in erythrocytes in the blood, and a reduction in the flow rate of the blood. Regarding PV, for example, poor blood supply to organs, headache due to hypoxia, dizziness, fatigue, bleeding due to the abnormality of platelet functions, and the like are observed. Moreover, regarding PV, skin itching caused by histamine release due to an increase in basophils, in particular, severe skin itching after taking a bath, may be generated. Furthermore, complications of PV may include: erythromelalgia exhibiting asymmetric swelling, pain, and burning sensations of hands and feet; thrombosis; and embolism. In some patients, PV transfers to acute myeloid leukemia (AML) or myelofibrosis (Non-Patent Document 6).

The prognosis of PV is favorable compared with other malignant tumors, and the duration of survival with the treatment is approximately 14 years (Non-Patent Document 7). At present, there are no drugs for healing PV, and the purposes of treating PV are mainly a reduction in the number of erythrocytes, the control of a hematocrit value to 45% or less, and prevention of thrombosis. The currently effective treatment methods for PV may include phlebotomy and cytoreductive therapy. However, these treatment methods have side effects such as iron deficiency or bone marrow suppression, and thereby reduce the QOL of patients. The satisfaction obtained from the current treatment methods for PV is low, and thus, it has been desired to develop a method for treating PV, which causes fewer side effects and improves the QOL of patients.

PRIOR ART DOCUMENTS

Non-Patent Documents

Non-Patent Document 1: P. Ponka, C. N. Lok, The transferrin receptor: role in health and disease, Int. J. Biochem. Cell Biol. 31 (1999) 1111-1137.

Non-Patent Document 2: D. R. Richardson, P. Ponka, The molecular mechanisms of the metabolism and transport of iron in normal and neoplastic cells, Biochim. Biophys. Acta 1331 (1997) 1-40.

Non-Patent Document 3: Daniels T R. Delgado T, Rodriguez J A, Helguera G, Penichet M L. The transferrin receptor part I: Biology and targeting with cytotoxic antibodies for the treatment of cancer. Clinical Immunology (2006) 121, 144-158

Non-Patent Document 4: J. E. Levy, O. Jin, Y. Fujiwara, F. Kuo, N. C. Andrews, Transferrin receptor is necessary for development of erythrocytes and the nervous system, Nat. Genet. 21 (1999) 396-399.

Non-Patent Document 5: Khatun R, Wu Y, Kanenishi K, Ueno M, Tanaka S, Hata T, Sakamoto H., Immunohistochemical study of transferrin receptor expression in the placenta of pre-eclamptic pregnancy, Placenta. 2003; 24(8-9): 870-6.

Non-Patent Document 6: Butcher C, D'Andrea R J. Molecular aspects of polycythemia vera (review). Int J Mol Med. 2000 September; 6(3): 243-52.

Non-Patent Document 7: Tefferi A, Rumi E, Finazzi G, Gisslinger H, Vannucchi A M, Rodeghiero F, Randi M L, Vaidya R, Cazzola M, Rambaldi A, Gisslinger B, Pieri L, Ruggeri M, Bertozzi I, Sulai N H, Casetti I, Carobbio A, Jeryczynski G, Larson D R, Müllauer L, Pardanani A, Thiele J, Passamonti F, Barbui T. Survival and prognosis among 1545 patients with contemporary polycythemia vera: an international study. Leukemia. 2013 September; 27(9): 1874-81

SUMMARY OF INVENTION

Object to be Solved by the Invention

It is an object of the present invention to provide a therapeutic drug for polycythemia.

Means for Solving the Object

The present inventors have conducted studies directed towards achieving the aforementioned object. As a result, the present inventors have found that polycythemia can be treated by using an antibody which recognizes the amino acid sequence at a certain position in human TfR, thereby completing the present invention.

Specifically, according to the present invention, the following inventions are provided.

(1) A therapeutic drug for polycythemia, comprising an antibody which recognizes the amino acids at positions 629 to 633 of a human transferrin receptor.

(2) The therapeutic drug for polycythemia according to (1), wherein the polycythemia is polycythemia vera.

(3) The therapeutic drug for polycythemia according to (1) or (2), which is used in combination with another polycythemia treatment method.

(4) The therapeutic drug for polycythemia according to any one of (1) to (3), wherein the antibody is an antibody having a heavy chain first complementarity determining region (VH CDR1), a heavy chain second complementarity determining region (VH CDR2), and a heavy chain third complementarity determining region (VH CDR3), which are as set forth in SEQ ID NOs: 1, 2, and 3, respectively, and also having a light chain first complementarity determining region (VL CDR1), a light chain second complementarity determining region (VL CDR2), and a light chain third complementarity determining region (VL CDR3), which are as set forth in SEQ ID NOs: 4, 5, and 6, respectively.

(5) The therapeutic drug for polycythemia according to any one of (1) to (4), wherein the antibody is an antibody having a heavy chain as set forth in SEQ ID NO: 7 and a light chain as set forth in SEQ ID NO: 8.

(6) The therapeutic drug for polycythemia according to any one of (1) to (5), wherein the antibody is a human antibody or a humanized antibody.

(7) The therapeutic drug for polycythemia according to any one of (1) to (6), wherein the antibody is an antibody fragment selected from the group consisting of Fab, Fab', $F(ab')_2$, a single-chain antibody (scFv), a dimerized V region (Diabody), a disulfide-stabilized V region (dsFv) and a peptide comprising CDR.

(8) The therapeutic drug for polycythemia according to any one of (1) to (7), which is used in combination with hydroxyurea.

(A) Provided is a method for treating polycythemia, which comprises administering to a subject, an antibody which recognizes the amino acids at positions 629 to 633 of a human transferrin receptor.

(B) An antibody which recognizes the amino acids at positions 629 to 633 of a human transferrin receptor, wherein the antibody is for use in the treatment of polycythemia.

(C) Use of an antibody which recognizes the amino acids at positions 629 to 633 of a human transferrin receptor, for the production of a therapeutic drug for polycythemia.

Advantageous Effects of Invention

The therapeutic drug for polycythemia of the present invention is useful in the treatment of polycythemia.

BRIEF DESCRIPTION OF DRAWINGS

FIG. 1 shows the sites of individual TfR mutant fragments, at which point mutations are introduced.

FIG. 2 shows the reactivity of TfR436 with soluble wild-type TfR (sTfR) and TfR mutant fragments.

FIG. 3 shows the Tf-TfR binding inhibitory activity of TfR436.

FIG. 4 shows inhibition of the growth of erythroblast cells by TfR436.

EMBODIMENT OF CARRYING OUT THE INVENTION

Hereinafter, the present invention will be described more in detail.

Definitions and General Techniques

Unless otherwise specified in the present description, scientific terms used regarding the present invention have meanings which are generally understood by a person skilled in the art. In general, nomenclatures and techniques applied to the cell and tissue culture, molecular biology, immunology, microbiology, genetics, protein and nucleic acid chemistry, and hybridization, which are described in the present description, are well known in the present technical field, and thus, are commonly used.

The methods and techniques of the present invention are carried out in accordance with conventional methods which are well known in the present technical field, in such ways as described in a variety of general reference documents cited and discussed throughout the present description and more specific reference documents, unless otherwise specified.

TfR

Human transferrin receptor (TfR) is a single-pass transmembrane protein (SEQ ID NO: 9) comprising 760 amino acids, and it is encoded by human chromosome 3. This protein has also been known as a CD71 antigen, and it is considered that this protein is associated with incorporation of iron into cells and cell growth. The TfR of the present invention is not particularly limited in terms of structure. Thus, human TfR includes all of a monomer, a polymer, an intact form expressed on a cell membrane, a soluble form constituted in an extracellular region, a truncated form, a mutation form caused by genetic mutation, deletion, etc., and a form which has undergone posttranslational modification by phosphorylation or the like.

React and Reactivity

The terms "react" and "reactivity" have the same meanings in the present description, unless otherwise specified. That is, these terms mean that an antibody recognizes an antigen. The antigen used herein may be any of an intact TfR expressed on a cell membrane, a truncated form, and a soluble form. In addition, the antigen may be either a TfR having a three-dimensional structure or a modified TfR. Examples of a means for examining reactivity include flow cytometry (FACS), enzyme-linked immunosorbent assay (ELISA), Western blotting, microfluorescence measuring technique (FMAT), surface plasmon resonance (Biacore), immunostaining, and immunoprecipitation.

The antibody used in flow cytometry may be either an antibody labeled with a fluorescent substance such as FITC or with biotin, or an unlabeled antibody. A fluorescently-labeled avidin, a fluorescently-labeled anti-human immunoglobulin antibody, or the like is used, depending on the presence or absence of labeling of the antibody used and the type thereof. Reactivity can be evaluated by adding a sufficient amount of anti-TfR antibody (generally having a final concentration of 0.01 to 10 μg/mL) to an analyte, and then by comparing the obtained reactivity with the reactivity with a negative control antibody or a positive control antibody.

Antibody

In the present description, the following abbreviations (in the parentheses) are used in accordance with the customs, as necessary.

Heavy chain (H chain), light chain (L chain), heavy chain variable region (VH), light chain variable region (VL), complementarity determining region (CDR), first complementarity determining region (CDR1), second complementarity determining region (CDR2), third complementarity determining region (CDR3), heavy chain first complementarity determining region (VH CDR1), heavy chain second complementarity determining region (VH CDR2), heavy chain third complementarity determining region (VH CDR3), light chain first complementarity determining region (VL CDR1), light chain second complementarity determining region (VL CDR2), and light chain third complementarity determining region (VL CDR3).

In the present description, the term "antibody" has the same definitions as immunoglobulin, and should be understood as generally known in the present technical field. Specifically, the term "antibody" is not limited by any given specific method for producing the antibody. For example, the term "antibody" includes, but is not limited to, a recombinant antibody, a monoclonal antibody, and a polyclonal antibody.

In the present description, the term "human antibody" is used to mean any given antibody, in which the sequences of a variable region and a constant region are human sequences. This term includes antibodies which have human sequences and are modified, for example, to remove cysteine which may cause a possible decrease in immunogenicity, an increase in affinity, and undesirable folding. This term also includes antibodies produced in non-human cells by recombination, which enable glycosylation which is not specific to human cells. These antibodies can be prepared in various ways.

In the present description, the term "humanized antibody" means a non-human-derived antibody, in which amino acid residues characteristic for a non-human antibody sequence are substituted with residues found in positions corresponding to those of a human antibody. This "humanization" process is considered to reduce the immunogenicity of the obtained antibody in human. It would be understood that a non-human-derived antibody can be humanized using a technique well known in the present technical field. Please refer to, for example, Winter et al., Immunol. Today 14: 43-46 (1993). The target antibody can be produced by an engineering approach via a recombination DNA technique of substituting CH1, CH2, CH3, a hinge domain, and/or a framework domain with those of the corresponding human sequence. For example, WO92/02190, and U.S. Pat. Nos. 5,530,101, 5,585,089, 5,693,761, 5,693,792, 5,714,350 and 5,777,085 can be referred. In the present description, the term "humanized antibody" includes a chimeric human antibody and a CDR-grafted antibody, within the definitions thereof.

The sequence of a framework region (FR) in a variable region of the antibody is not particularly limited, unless it substantially affects the specific binding ability of the antibody to the corresponding antigen. The FR region of a human antibody is preferably used, but it is also possible to use FR regions of animal species other than humans (e.g. a mouse or a rat).

In one aspect, the antibody comprises a constant region as well as a variable region (e.g. IgG antibody). The sequence of such a constant region is not particularly limited. For example, the constant region of a known human antibody can be used. The heavy chain constant region (CH) of a human antibody is not particularly limited, as long as it belongs to a human immunoglobulin (hereinafter referred to as "hIg"). Those of hIgG class are preferable, and any one of subclasses belonging to hIgG class, such as hIgG1, hIgG2, hIgG3 or hIgG4, may be used. On the other hand, the light chain constant region (CL) of a human antibody is not particularly limited, as long as it belongs to hIg, and those of κ class or λ class can be used. In addition, constant regions of animal species other than humans (e.g. a mouse or a rat) can also be used.

In the present description, the term "modified body" or "modified antibody" is used to mean that the amino acid sequence of the variable region (CDR sequences and/or FR sequences) of a parent antibody comprises a substitution, deletion, addition and/or insertion of one or multiple amino acids.

In the present description, the "parent antibody" means a TfR436 antibody which has a VH comprising the amino acid sequence as set forth in SEQ ID NO: 7 and a VL comprising the amino acid sequence as set forth in SEQ ID NO: 8. In the amino acid sequence, one or several (for example, 1 to 8, preferably 1 to 5, more preferably 1 to 3, and particularly preferably 1 or 2) amino acids are deleted, added, substituted and/or inserted. As a method of preparing the amino acid sequence of an antibody having a binding ability to TfR, which has been well known to a person skilled in the art, a method of introducing a mutation into a protein has been known. For instance, such a skilled person could prepare a modified antibody functionally equivalent to an antibody having a TfR-binding activity by appropriately introducing a mutation into the amino acid sequence of the antibody having a TfR-binding activity according to a site-directed mutagenesis (Hashimoto-Gotoh, T, Mizuno, T, Ogasahara, Y, an DNA kagawa, M. (1995) An oligodeoxyribonucleotide-directed dual amber method for site-directed mutagenesis. Gene 152, 271-275, Zoller, M J, and Smith, M. (1983) Oligonucleotide-directed mutagenesis of DNA fragments cloned into M13 vectors. Methods Enzymol. 100, 468-500, Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456, Kramer W, and Fritz H J (1987) Oligonucleotide-directed construction of mutations via gapped duplex DNA Methods. Enzymol. 154, 350-367, Kunkel, T A (1985) Rapid and efficient site-specific mutagenesis without phenotypic selection. Proc Natl Acad Sci USA. 82, 488-492). Thus, an antibody comprising a mutation of one or several amino acids in the variable region or constant region of a parent antibody and having a binding activity to TfR can also be used.

In the present description, the phrase "an activity equivalent to the activity of the parent antibody" is used to mean that the human TfR-binding activity of a certain antibody is equivalent to that of the parent antibody thereof. The term "equivalent" does not necessarily mean the same level of activity. The activity may be increased, or the activity may also be decreased, as long as the antibody has the activity. An antibody having a decreased activity may be an antibody having an activity that is, for example, 30% or more, preferably 50% or more, more preferably 80% or more, further preferably 90% or more, and particularly preferably 95% or more of the activity of the original antibody.

The term "binding activity" means the activity of an antibody to recognize an antigen. This antigen may be an intact TfR expressed on a cell membrane, a truncated form, or a soluble form. In addition, the antigen may be either a TfR having a three-dimensional structure or a modified TfR. Examples of a means for examining the binding activity include flow cytometry (FACS), enzyme-linked immunosorbent assay (ELISA), Western blotting, microfluorescence measuring technique (FMAT), and surface plasmon resonance (Biacore).

The Tf-TfR binding inhibitory activity of an antibody can be measured according to the method described in the after-mentioned "Example 2(2): Comparison between TfR436 antibody and antibodies of other companies in terms of Tf-TfR binding inhibition." A TfR solution is dispensed into a substrate (a 96-well plate, etc.) and is then left at rest to obtain a solid phase, and thereafter, blocking is carried out. Subsequently, an HRP-labeled Tf solution is dispensed into the substrate, and an antibody is further added thereto, so that they are allowed to react with each other at room temperature. Thereafter, the substrate is washed, and a coloring reagent (TMB, etc.) is then added thereto, so that they are allowed to react with each other. After that, the absorbance is measured using a plate reader. By performing the above-described operations, the Tf-TfR binding inhibitory activity of the antibody can be evaluated.

The antibody is not limited by its origin, and it may be an antibody derived from any animal, such as a human antibody, a mouse antibody, or a rat antibody. Also, the present antibody may be a chimeric antibody or a humanized antibody. In a preferred aspect, the antibody of the present invention is a human antibody.

The antibodies may be different from one another in terms of amino acid sequence, molecular weight, isoelectric point, the presence or absence of a sugar chain or the form thereof, etc., depending on the after-mentioned cells or hosts which produce the antibodies, or a purification method. For example, an antibody which undergoes a posttranslational modification on the amino acid sequence described in the present description is included in the present invention. Moreover, an antibody which undergoes a posttranslational modification on a site other than those for the known posttranslational modification is also included in the present invention. Furthermore, when the antibody is allowed to express in prokaryotic cells such as *Escherichia coli*, a methionine residue is added to the N-terminus of the amino acid sequence of the original antibody. Such an antibody may also be used in the present invention. An antibody which undergoes a posttranslational modification on a site other than those for the known posttranslational modification is also included in the present invention.

Production of Antibody (1) Production of scFv Reacting with Antigen Using Phage Display Library The antibody can be prepared by several methods known in the present technical field. For example, using a phage display technique, a library comprising a repertoire of antibodies having various affinity for TfR can be provided. Subsequently, such a library can be screened to identify and isolate antibodies against TfR. Preferably, the phage library is a scFv phage display library which is generated using human VL and VH cDNA which has been prepared from mRNA isolated from human B cells. A method of preparing and screening such a library is known in the present technical field. A genetic substance is recovered from phage clones exhibiting reactivity which have been screened using a human TfR as an antigen. By analyzing the selected phage gene, the DNA sequences of VH and VL encoding the variable region of a human antibody binding to the antigen can be determined. Using this scFv sequence, IgG is prepared from scFv, so as to obtain a human antibody.

(2) Preparation of IgG from scFv (Preparation of Human Antibody)

An H chain or L chain expression vector is produced, and it is then allowed to express in a host cell. Thereafter, the secreted supernatant is recovered and is then purified, so as to obtain a human antibody. Alternatively, such a human antibody can also be obtained by allowing VH and VL to express in a single vector (tandem type). These methods are well known, and can be carried out with reference to WO92/01047, WO92/20791, WO93/06213, WO93/11236, WO93/19172, WO95/01438, WO95/15388, WO97/10354, etc.

Specifically, DNA encoding VH is ligated to another DNA molecule encoding a heavy chain constant region (CH1, CH2 and CH3), so as to obtain a full-length heavy chain gene. The sequence of a human heavy chain constant region gene is known in the present technical field (for example, Kabat, E. A. et al., (1991) Sequences of Proteins of Immunological Interest, 5th edition, U. S. Department of Health and Human Services, NIH Publication No. 91-3242), and a DNA fragment including such a region can be obtained by standard PCR amplification. The heavy chain constant region may be the constant region of IgG I, IgG2, IgG3, IgG4, IgA, IgE, IgM or IgD. The most preferred constant region is that of IgG1 or IgG2. The constant region sequence of IgG1 may include any given various alleles or allotypes known to be generated among different individuals, such as Gm (1), Gm (2), Gm (3) or Gm (17). These allotypes correspond to a substitution of amino acids naturally-occurring in the constant region of IgG1.

DNA encoding VL is ligated to another DNA molecule encoding the light chain constant region CL, so as to obtain a full-length L chain gene (and a Fab light chain gene). The sequence of a human light chain constant region gene is known in the present technical field (for example, Kabat, E. A. et al., (1991) Sequences of Proteins of Immunological Interest, $5^{th}$ edition, U. S. Department of Health and Human Services, NIH Publication No. 91-3242), and a DNA fragment including such a region can be obtained by standard PCR amplification. The light chain constant region may be the constant region of κ or λ. The κ constant region may include any given various alleles known to be generated among different individuals, such as Inv (1), Inv (2) or Inv (3). The λ constant region may be derived from any one of the three λ genes.

The thus obtained DNA encoding an H chain or L chain is inserted into a vector to produce an expression vector, and the produced expression vector is then allowed to express in a host cell. Thereafter, the secreted supernatant is recovered and purified to obtain a human antibody. Examples of the expression vector include a plasmid, retrovirus, adenovirus, adeno-associated virus (AAV), plant viruses such as cauliflower mosaic virus or tobacco mosaic virus, a cosmid, YAC, and EBV-derived episome. An expression vector and an expression regulatory sequence are selected, so that they are suitable for a host cell used for expression. An antibody light chain gene and an antibody heavy chain gene can be inserted into different vectors, or the two genes can also be inserted into a single expression vector. An antibody gene is inserted into an expression vector by a standard method (for example, ligation of a complementary restriction site on an antibody gene fragment to a vector, or blunt-ended ligation applied when no restriction sites are present).

A favorable vector encodes a functionally completed human CH or CL immunoglobulin sequence having a suitable restriction site, which has been produced by an engineering approach such that any given VH or VL sequence can be easily inserted and then expressed therein, as described above. In such a vector, splicing generally takes place between a splice donor site in the inserted J region and a splice acceptor site preceding a human C domain, or such splicing also takes place in a splice region existing in a human CH exon. Polyadenylation and transcription termination take place in a natural chromosomal site downstream of a coding region. A recombinant expression vector can also encode a signal peptide which promotes the secretion of an antibody chain derived from a host cell. An antibody chain gene can be cloned into a vector, such that a signal peptide can be ligated in-frame to the amino terminus of an immunoglobulin chain. The signal peptide may be either an immunoglobulin signal peptide or a heterogeneous signal peptide (namely, it may be a non-immunoglobulin protein-derived signal peptide).

An expression vector used for the antibody of the present invention may also have sequences such as a sequence for regulating replication of the vector in a host cell (e.g. a replication origin) or a selective marker gene sequence, as well as an antibody gene and a regulatory sequence. The selective marker gene promotes selection of a host cell into which a vector has been introduced. For instance, the selective marker generally imparts resistance to drugs such as G418, hygromycin or methotrexate to a host cell into which the vector has been introduced. Preferred selective marker genes include a dihydrofolate reductase (DHFR) gene (used in selection/amplification of methotrexate as a dhfr-host cell), a neomycin phosphotransferase gene (used in selection of G418), and a glutamate synthase gene.

A host cell is transformed with an antibody gene expression vector produced by the above-described method. Any type of cell may be used as a host cell, as long as it can produce the present antibody. Examples of such a host cell include bacteria, yeast, animal cells, insect cells, and plant cells. Among these cells, animal cells are preferable. Examples of the animal cells include Chinese hamster ovary cells CHO/dhfr(−) and CHO/DG44, monkey-derived cells COS (A. Wright & S. L. Morrison, J. Immunol. 160, 3393-3402 (1998)), and SP2/O cells (mouse myeloma) (K. Motmans et al., Eur. J. Cancer Prev. 5, 512-5199 (1996), R. P. Junghans et al., Cancer Res. 50, 1495-1502 (1990)). For transformation, a lipofectin method (R. W. Malone et al., Proc. Natl. Acad. Sci. USA 86, 6007 (1989), P. L. Feigner et al., Proc. Natl. Acad. Sci. USA 84, 7413 (1987)), an electroporation method, a calcium phosphate method (F. L. Graham & A. J. van der Eb, Virology 52, 456-467 (1973)), a DEAE-Dextran method, and the like are preferably applied.

A transformant is cultured, and a human antibody is then separated from the cells of the transformant or a culture medium thereof. For separation/purification of the antibody, methods such as centrifugation, ammonium sulfate fractionation, salting-out, ultrafiltration, affinity chromatography, ion exchange chromatography and gel filtration chromatography can be used by appropriately combining them.

Antibody Fragments

An antibody fragment can be produced based on the present antibody, or based on the sequence information of a gene encoding the present antibody. Examples of the antibody fragment include Fab, Fab', $F(ab')_2$, scFv, and dsFv antibodies.

Fab is obtained by digesting IgG by papain in the presence of cysteine. It is an antibody fragment with a molecular weight of approximately 50,000, which is constituted with L chain and H chain variable regions, and an H chain fragment consisting of a CH1 domain and a portion of a hinge region. In the present invention, the above-described antibody can be obtained by papain digestion. In addition, Fab can also be prepared by incorporating DNA encoding a portion of the H chain and the L chain of the above-described antibody into a suitable vector, then performing transformation with the resulting vector, and then obtaining it from the transformant.

Fab' is an antibody fragment with a molecular weight of approximately 50,000, which is obtained by cleaving a disulfide bond between the H chains of the below-mentioned $F(ab')_2$. In the present invention, Fab' can be obtained by digesting the above-described antibody by pepsin, and then cleaving a disulfide bond with a reducing agent. In addition, as with Fab, Fab' can also be prepared by genetic engineering using DNA encoding the Fab'.

$F(ab')_2$ is an antibody fragment with a molecular weight of approximately 100,000, which is obtained by binding, via a disulfide bond, one fragment (Fab') constituted with L chain and H chain variable regions and an H chain fragment consisting of a CH1 domain and a portion of a hinge region, to the other fragment (Fab'). In the present invention, $F(ab')_2$ can be obtained by digesting the above-described antibody by pepsin. In addition, as with Fab, $F(ab')_2$ can also be prepared by genetic engineering using DNA encoding the $F(ab')_2$.

scFv is an antibody fragment obtained by ligating the C-terminus of one chain of Fv consisting of an H chain variable region and an L chain variable region to the N-terminus of the other chain thereof, using a suitable peptide linker, so as to form a single chain. $(GGGGS)_3$ (SEQ ID NO: 11) having high flexibility can be used, for example, as such a peptide linker. For instance, DNA encoding the H chain variable region and L chain variable region of the above-described antibody and DNA encoding a peptide linker are used to construct DNA encoding a scFv antibody, and the thus constructed DNA is then incorporated into a suitable vector. Thereafter, scFv can be prepared from a transformant obtained by transformation with the aforementioned vector.

dsFv is an Fv fragment obtained by introducing a Cys residue into a suitable site in each of an H chain variable region and an L chain variable region, and then stabilizing the H chain variable region and the L chain variable region by a disulfide bond. The site in each chain, into which the Cys residue is to be introduced, can be determined based on a conformation predicted by molecular modeling. In the present invention, for example, a conformation is predicted from the amino acid sequences of the H chain variable region and L chain variable region of the above-described antibody, and DNA encoding each of the H chain variable region and the L chain variable region, into which a mutation has been introduced based on such prediction, is then constructed. The thus constructed DNA is incorporated into a suitable vector. Thereafter, dsFv can be then prepared from a transformant obtained by transformation with the aforementioned vector.

Further, it is also possible to ligate the scFv antibody to the dcFv antibody or the like using a suitable linker, or to fuse such an antibody fragment with streptavidin, so as to multimerize the antibody fragment.

Pharmaceutical Composition and Preparation

A pharmaceutical composition and a preparation, each comprising the therapeutic drug for polycythemia of the present invention, are also included in the scope of the present invention.

The therapeutic drug for polycythemia of the present invention can be used to treat polycythemia.

Polycythemia means a state in which the blood cell volume is absolutely or relatively increased, and a majority of such blood cells are erythrocytes. Hence, polycythemia has almost the same concept as erythrocythemia. Polycythemia includes polycythemia vera, relative polycythemia, and secondary polycythemia.

Polycythemia vera is one type of myeloproliferative neoplasm, which is a disease in which absolute increases in the blood erythrocyte count and in the circulating blood volume occur due to cell proliferation caused by the acquired genetic abnormality of hematopoietic stem cells. In the case of polycythemia vera, leukocytes and platelets are also increased, and thus, whole blood cells are often increased.

Relative polycythemia means a state in which the total volume of erythrocytes is not increased, but the volume of erythrocytes per blood unit volume is relatively increased due to a reduction in plasma as a liquid component which generally accounts for a half or more of blood components.

Secondary polycythemia is also referred to as deuteropathic erythrocythemia, and it is a state in which erythropoiesis reacts with an increase in the volume of erythropoietin as a hematopoietic factor by some cause, and the volume of erythrocytes is thereby increased.

The polycythemia in the present invention is preferably polycythemia vera.

The therapeutic drug for polycythemia of the present invention may be used in combination with another polycythemia treatment method.

Examples of such another polycythemia treatment method may include phlebotomy, chemical therapy (anti-cancer agents, etc.), and anti-platelet agents.

Phlebotomy is a therapy by which blood is withdrawn and discarded.

Examples of the chemotherapeutic agent may include hydroxycarbamide (hydroxyurea, product name: HYDREA), ranimustine (product name: Cymerin), busulfan (product name: MABLIN POWDER), and ruxolitinib (product name: Jakavi).

The anti-platelet agent may be a low-dose aspirin, etc.

Preferably, the therapeutic drug for polycythemia of the present invention can be used in combination with hydroxyurea.

A pharmaceutical composition and a preparation, each comprising the therapeutic drug for polycythemia of the present invention, preferably comprises a physiologically acceptable diluent or carrier, in addition to the antibody. The pharmaceutical composition or the preparation may also be a mixture with other drugs. Examples of a suitable carrier used herein may include a normal saline, a phosphate buffered saline, a phosphate buffered saline with glucose, and a buffered saline, but the examples are not limited thereto. Otherwise, the antibody is freeze-dried, and when needed, the aforementioned buffered aqueous solution may be added thereto to reconstitute the antibody, and the thus reconstituted antibody may be then used. Examples of the dosage form of the preparation may include: oral administration, which uses a tablet, a capsule, a granule, a powder agent, a syrup, etc.; and parenteral administration, which includes injections (subcutaneous injection, intravenous injection, intramuscular injection, intraperitoneal injection, etc.), percutaneous administration, transmucosal administration, transnasal administration, transpulmonary administration, the use of a suppository, etc. The preparation comprising the pharmaceutical composition of the present invention may be administered alone, or it may also be used in combination with other drugs.

The applied dose of the therapeutic drug for polycythemia of the present invention is different depending on symptom, age, body weight, etc. In general, in the case of oral administration, the present pharmaceutical composition is administered at a dose of approximately 0.01 mg to 1,000 mg per day per adult, in terms of the amount of an antibody contained therein. Such a dose can be administered once or divided over several administrations per day. On the other hand, in the case of parenteral administration, the present pharmaceutical composition can be administered at a dose of approximately 0.01 mg to 1,000 mg for a single administration via subcutaneous injection, intramuscular injection or intravenous administration.

The present invention will be described in more detail in the following examples. However, these examples are not intended to limit the scope of the present invention.

EXAMPLES

In the following examples, the TfR436 antibody described in paragraphs 0090 and 0091 of International Publication WO2014/073641 was used.

The CDR sequences of the TfR436 antibody will be shown below.

```
VH CDR1:
                    (SEQ ID NO: 1)
SYGMH

VH CDR2:
                    (SEQ ID NO: 2)
VISYDGSNKYYADSVKG

VH CDR3:
                    (SEQ ID NO: 3)
DSNFWSGYYSPVDV

VL CDR1:
                    (SEQ ID NO: 4)
TRSSGSIASNSVQ

VL CDR2:
                    (SEQ ID NO: 5)
YEDTQRPS

VL CDR3:
                    (SEQ ID NO: 6)
QSYDSAYHWV
```

The VH sequence and VL sequence of the TfR436 antibody will be shown below.

```
TfR436 VH
                                        (SEQ ID NO: 7)
DVQLVQSGGGVVQPGRSLRLSCAASGFPFKSYGMHWVRQAPGKGLEWVAV

ISYDGSNKYYADSVKGRFTISRDNSKNTLYLQMNSLRGEDTAVYYCARDS

NFWSGYYSPVDVWGQGTTVTVSS

TfR436 VL
                                        (SEQ ID NO: 8)
NFMLTQPHSVSESPGKTVTISCTRSSGSIASNSVQWYQQRPGSAPITVIY

EDTQRPSGVPDRFSGSIDSSSNSASLTISGLQTEDEADYYCQSYDSAYHW

VFGGGTKLAVL
```

Example 1: Identification of Binding Site of TfR436 Antibody

The TfR436 antibody did not cross-react with mouse TfR, but it exhibited cross-reactivity with hamster TfR. The amino acid sequence of a transferrin (TF)-binding site (the amino acids at positions 569 to 760) in TfR was aligned. The amino acids of a human TfR sequence, which were the same as hamster but were different from mouse, were picked up. The picked amino acids were subjected to point mutation, as shown in FIG. 1, so that soluble TfR mutant fragments were produced.

(1) Production of Soluble Wild-Type TfR (sTfR) and TfR Mutant Fragments (MF1 to MF7)

A human TfR extracellular domain (the amino acids at positions 89 to 760) or each TfR mutant fragment (MF1 to MF7) as shown in FIG. 1, and a nucleotide sequence encoding AAARGGPEQKLISEEDLNSAVDHHHHHH (SEQ ID NO: 10) were totally synthesized. A neomycin resistance gene and a DHFR gene were incorporated into the expression vector pCAGGS (Non-Patent Document 2: Niwa et al. 1991), and thereafter, the synthesized genes were each inserted into the multicloning site of the obtained expression vector, so as to produce a pCAGGS-Neo-DHFR-sTFR-myc-his expression plasmid. Using Expifectamine (Invitrogen), the Expi293 cells (Invitrogen) were transfected with the above-described plasmid, and were then cultured at 37° C. in 8% $CO_2$ at 135 rpm for 5 days. Thereafter, a culture supernatant was recovered by centrifugation. A HisTrapHP (GE Healthcare) column was connected with AKTA prime (GE Healthcare), and sTfR or MF1 to MF7 were then purified using 20 mM Imidazole/DPBS as a binding buffer and 500 mM Imidazole/DPBS as an elution buffer. The eluted protein was subjected to buffer exchange with 30 mM HEPES, 5% trehalose, pH 7.2, by using a Zeba spin column (Thermo scientific).

(2) Identification of Binding Site of TfR436 Antibody

The thus purified sTfR or MF1 to MF7 were diluted with PBST (Phosphate Buffered Saline with Tween 20, TaKaRa), and the diluted solutions were prepared at 7 stages by 3-fold dilution from 600 ng/mL. Thereafter, the diluted solution was dispensed into Ni-NTA HisSorb Strips 96-well plate (QIAGEN) in an amount of 100 μL/well, and the plate was then placed on a shaker, followed by performing a reaction at room temperature. One hour later, the reaction mixture was washed with PBST Buffer 5 times, and the TfR436 antibody (1 ug/mL) was dispensed into the 96-well plate in an amount of 100 μL/well. The plate was placed on a shaker, and a reaction was then performed at room temperature for 1 hour. Thereafter, the reaction mixture was washed with PBS-T Buffer 5 times, and a 50,000-fold diluted secondary antibody, $F(ab')_2$ Fragment Anti-Human IgG Fcγ (Jackson Immuno Research), was then dispensed into the 96-well plate in an amount of 100 μL/well, followed by performing a reaction at room temperature for 1 hour. The reaction mixture was washed with PBST Buffer 5 times, and TMB Soluble Reagent (High Sensitivity) (Scy Tek) was then dispensed into the plate in an amount of 100 μL/well, followed by performing a reaction at room temperature in a dark place for 3 minutes. After that, TMB Stop Buffer (Scy Tek) was added to the plate in an amount of 100 μL/well, and the obtained mixture was then shaken using a shaker for 1 minute. Thereafter, the absorbance at 450 nm (ref. 620 nm) was measured using a plate reader.

As a result, as shown in FIG. 2, a reduction in the reactivity of the TfR436 antibody with the TfR mutant fragment MF5 was observed, but a reduction in the reactivity of the TfR436 antibody with other mutant fragments was not observed. That is to say, when the amino acids at positions 629, 630 and 633 of TfR are substituted with other amino acids, the TfR436 antibody cannot recognize the TfR. Thus, it was suggested that the amino acids at positions 629 to 633 of TfR should be an epitope recognized by the TfR436 antibody.

Example 2: Comparison Between TfR436 Antibody and Comparative Antibodies in Terms of Tf-TfR Binding Inhibition (1) Production of Comparative Antibody A24

Patent Document US2008/0193453 discloses an A24 antibody reacting against human TfR. In order to compare the TfR436 antibody with the A24 antibody, the deposited hybridomas were acquired, and the antibody was produced. Specifically, the hybridomas were seeded into RPMI1640 (GIBCO) supplemented with 10% FBS at a cell concentration of 1 to $2\times10^5$/mL, and were then cultured in a 5% $CO_2$ incubator at 37° C. After completion of an expansion culture, the cells were recovered by centrifugation, and were then washed with PBS twice. Thereafter, the resulting cells were further subjected to an expansion culture in a serum-free medium Cosmedium 005 (Cosmo Bio Co., Ltd.) and 0.5% Nutridoma-CS (Roche) to result in a volume of 550 mL. Five days after the cells became confluent, a culture supernatant was recovered by centrifugation.

The recovered supernatant was applied onto a protein A carrier (Ab-Capcher ExTra: ProteNova), and an antibody binding to protein A was eluted with a 0.1 M glycine-HCl buffer (pH 2.7), and then, was rapidly neutralized with a 1 M Tris-HCl buffer (pH 8.5). Thereafter, using an Ultracell Ultrafiltration Disk (Merck Millipore), the buffer was exchanged with PBS.

(2) Comparison Between TfR436 Antibody and Antibodies of Other Companies in Terms of Tf-TfR Binding Inhibition The sTfR described in Example 1 was adjusted to a concentration of 5.0 μg/mL by addition of PBST, and the diluted solution was then dispensed into MaxiSorp 96-well plate (Nunc) in an amount of 100 μL/well. Thereafter, it was left at rest at 4° C. overnight to obtain a solid phase. On the following day, the solid phase solution was discarded, and 100% Block Ace (DS Pharma Biomedical) was added to the plate in an amount of 200 μL/well, followed by leaving the obtained mixture at rest at room temperature so as to carry out blocking. One hour later, the reaction mixture was washed with PBST Buffer 5 times, and HRP-labeled Tf (2 ug/mL) was then dispensed into the plate in an amount of 50 μL/well. Thereafter, the TfR436 antibody, the A24 antibody (2-fold dilution series from 10 μg/mL), or holo-Tf (Sigma) (2-fold dilution series from 300 μg/mL) was further added to the mixture in an amount of 50 μL/well. The obtained mixture was reacted at room temperature for 1 hour, and was then washed with PBST Buffer 5 times. Thereafter, TMB Soluble Reagent (High Sensitivity) was dispensed into the plate in an amount of 100 μL/well, and the obtained mixture was then reacted at room temperature in a dark place. Twenty five minutes later, TMB Stop Buffer was added to the plate in an amount of 100 μL/well, and the obtained mixture was shaken with a shaker for 1 minute. Thereafter, the absorbance at 450 nm (ref. 620 nm) was measured.

As a result, as shown in FIG. 3, the TfR436 antibody completely inhibited the binding of Tf-TfR at a significantly low dose (100 ng/mL). In contrast, the A24 antibody could not completely inhibit the binding of Tf-TfR, even though it was used at a dose of 10 μg/mL, and could inhibit only 50% of the Tf-TfR binding. Thus, it was suggested that the TfR436 antibody is excellent in terms of inhibition of the Tf-TfR binding.

Example 3: Effect of Inhibiting EPO-Independent Erythroblast Differentiation in PV Patient-Derived Hematopoietic Stem Cells PV patient-derived hematopoietic stem cells are characterized in that BFU-E or CFU-E is formed in the cells even in the absence of erythropoietin (EPO). The activity of TfR436 to inhibit the formation of these colonies was examined.

(1) PBMC Separation

The peripheral blood of a PV patient, which had been obtained by phlebotomy, was dispensed into three 50-mL centrifuge tubes in an amount of 20 mL each, and an equal amount of PBS (Gibco) was then added to each tube, followed by mixing. Thereafter, 15 mL of LymphoSep, Lymphocyte Separation Media (MP Biomedicals™) was dispensed into four novel 50-mL centrifuge tubes, and the peripheral blood diluted with PBS was then slowly added thereto in an amount of 30 mL each, and the obtained mixture was then centrifuged at 1,500 rpm at room temperature for 30 minutes. After completion of the centrifugation, the plasma as a supernatant was removed, and a PBMC layer was collected by transfer pipetting. The collected PBMC layer was suspended in 20 mL of PBS+2% FBS (Gibco). The thus obtained suspension was further centrifuged at 1350 rpm at room temperature for 10 minutes, a supernatant was then removed, and the residue was then suspended in 1 to 5 mL of IMDM (Nacalai Tesque)+2% FBS. Using 0.2% Trypan Blue, the number of cells was counted, and the cells were adjusted to $2\times10^6$ cells/mL by addition of IMDM+2% FBS.

(2) Colony Assay

TfR436 and a human IgG1 antibody used as a negative control were each diluted with IMDM+2% FBS to an antibody concentration of 10 to 1000 mg/mL. MethoCult™ H4534 Classic WithoutEPO (STEMCELL TECHNOLOGIES) was dispensed into seven 14-mL round bottle tubes in an amount of 3 mL each, and 300 jut of the above-prepared PBMC was then added thereto. Thereafter, an antibody-diluted solution or 3.3 μL of IMDM+2% FBS (control) was further added thereto, followed by full mixing. Thereafter, the reaction mixture was seeded on two 35-mm culture dishes in an amount of 1 mL each. This mixture was cultured at 37° C. in a 5% $CO_2$ incubator for 14 days. After completion of the culture, the 35-mm culture dishes were observed under a microscope, and the number of the formed BFU-E or CFU-E colonies was then counted. The colony formation percentage with respect to the number of colonies obtained by a culture without addition of antibodies was then calculated. As a result, the formation of erythroblast colonies was almost completely inhibited by addition of 100 ng/mL or more TfR436 (Table 1).

TABLE 1

Inhibition of PV patient-derived hematopoietic stem cell erythroblast colony formation by TfR436

| Sample | Conc. (ng/mL) | pt No. 1 | pt No. 2 | pt No. 3 | pt No. 9 | pt No. 11 | pt No. 13 | pt No. 14 | pt No. 15 |
|---|---|---|---|---|---|---|---|---|---|
| Human | 10 | 85.7% | 75.9% | 141.7% | 76.5% | 92.3% | 46.5% | 87.6% | 76.7% |
| IgG1 | 100 | 78.6% | 79.3% | 118.8% | 89.8% | 110.3% | 36.6% | 98.4% | 86.7% |
| | 1000 | 124.3% | 131.7% | 106.3% | 78.6% | 128.2% | 42.3% | 93.6% | 53.3% |
| TfR436 | 10 | 87.1% | 149.0% | 91.7% | 63.3% | 80.8% | 35.2% | 68.9% | 6.7% |
| | 100 | 0.0% | 2.1% | 0.0% | 0.0% | 0.0% | 23.9% | 0.0% | 0.0% |
| | 1000 | 0.0% | 0.0% | 0.0% | 1.0% | 0.0% | 19.7% | 0.0% | 3.3% |

| Sample | Conc. (ng/mL) | pt No. 7 | pt No. 18 | pt No. 20 |
|---|---|---|---|---|
| Human | 10 | 136.4% | 66.7% | 134.4% |
| IgG1 | 100 | 27.3% | 85.7% | 140.6% |
| | 1000 | 218.2% | 71.4% | 156.3% |
| TfR436 | 10 | 63.6% | 47.6% | 143.8% |
| | 100 | 0.0% | 0.0% | 0.0% |
| | 1000 | 0.0% | 0.0% | 0.0% |

Example 4: Effect of Suppressing Growth of Normal Erythroblast Cells

Frozen CD34-positive cells (POIETICS) were thawed at 37° C., and were then suspended in IMDM (GIBCO)+30% FBS (Sigma-Aldrich) and 100 U/ml DNase (QIAGEN), and thereafter, the cells were frozen and thawed according to the instructions of the manufacturer. Thereafter, the cells were adjusted to $5\times10^4$ cells/ml with a culture medium prepared by adding 2-ME (50 μmol/L) (GIBCO), hIL-3 (100 U/ml) (Milteny biotec), hEPO (4 U/ml) (Roche), and hSCF (50 ng/ml) (Peprotech) to an SF-03 medium (EIDIA Co., Ltd.). The resulting cells were dispensed into a 24-well plate in an amount of 1 ml/well, and were then cultured at 37° C. in a 5% $CO_2$ incubator. Seven days later, the cells were seeded into a 96-well plate, and the antibody was then added thereto in an amount of 0.15 ng/mL to 10 μg/mL, followed by culturing the mixture. A well without addition of the antibody was used as a control. Ninety six hours later, each well was fully stirred by pipetting, and 150 μl of the cell lysate was transferred into a V-bottom plate. Then, 20 μl of the transferred cell lysate was absorbed by FACS Calibur, and the number of cells was then counted. The value obtained by multiplying the obtained cell number by 10 was set to be the number of cells per well, and the growth percentage of the cells at each concentration of the antibody was then calculated, while the mean value of the control was set to be 100%. As a result, TfR436 suppressed the growth of erythroblast cells (FIG. 4). $GI_{50}$ was 125 ng/mL.

Example 5: Inhibition of Erythroblast Colony Formation in Hematopoietic Stem Cells Derived from Patients Administered with HYDREA™ (Hydroxyurea)

Hematopoietic stem cells derived from patients administered with HYDREA™ were used as PV patient-derived hematopoietic stem cells, and the activity of TfR436 to inhibit erythroblast colony formation was examined by the same method as that of Example 3. Besides, HYDREA™ was administered as hydroxycarbamide (also referred to as "hydroxyurea") to the patients via oral administration at a daily dose of 500 mg to 2000 mg once or divided over twice or three times. As a result, erythroblast colony formation was inhibited by addition of 100 ng/ml or more TfR436 (Table 2).

TABLE 2

Inhibition of erythroblast colony formation of HYDREA ™ administered patient-derived hematopoietic stem cells by TfR436

| Sample | Conc. (ng/mL) | pt No. 1 | pt No. 23 | pt No. 24 | pt No. 26 | pt No. 27 | pt No. 28 |
|---|---|---|---|---|---|---|---|
| Human | 10 | 227.3% | 100.0% | 123.5% | 123.1% | 114.3% | 118.8% |
| IgG1 | 100 | 263.6% | 114.4% | 131.4% | 91.5% | 266.7% | 125.0% |
| | 1000 | 181.8% | 116.7% | 76.5% | 204.3% | 147.6% | 75.0% |
| TfR436 | 10 | 109.1% | 100.0% | 68.6% | 148.9% | 152.4% | 112.5% |
| | 100 | 0.0% | 0.0% | 0.0% | 10.6% | 0.0% | 0.0% |
| | 1000 | 0.0% | 0.0% | 0.0% | 0.0% | 0.0% | 0.0% |

Example 6: Combined Effects of TfR436 and Hydroxyurea

HEL cells were cultured in an RPMI-1640 (Sigma-Aldrich)+10% FBS (Sigma-Aldrich)+1% PenStrep (Gibco) medium, and were then adjusted to 20000 cells/mL with the same medium as described above. Hydroxyurea (Wako Pure Chemical Industries, Ltd.) was weighed and was then dissolved in a concentration of 100 mM in distilled water for injection (Otsuka Pharmaceutical). The thus adjusted cell solution was seeded on a 96-well plate (Thermo SCIENTIFIC) in an amount of 100 μL/well. TfR436 (150, 300, 600, and 1200 ng/mL) and hydroxyurea (125, 250, 500, and 1000 μM), which had been each adjusted to a concentration which was 4 times the final concentration with the above-described medium, were added, alone or in combination, in an amount of 50 μL each. Thereafter, the medium was further added in an amount of 50 μL each into wells containing only the drug, and in an amount of 100 μL each into cell growth control wells. The thus prepared plate was then cultured 37° C. in a 5% $CO_2$ incubator for 72 hours.

From the plate after completion of the culture, the cultured cells in each well were dispensed into a V-bottom plate (Costar) in an amount of 100 μL, while pipetting. Thereafter, 10 μL of a PI (BD) solution which had been 20 times diluted with FACS Buffer (self-prepared; PBS supplemented with 1% BSA, 2 mM EDTA, and 0.1% $NaN_3$) was added to the V-bottom plate. The obtained mixture was set into HTS of FACS Calibur (BD), and 20 μL of the cells in each well was absorbed. Then, the fluorescence of FL2 and the number of cells were measured. From the obtained results, the number of living cells (PI negative) and the number of dead cells (PI positive) were calculated, and thereafter, Viability (the number of PI-negative cells/the total number of cells×100) (%) and cell death percentage (100−Viability) (%) were calculated. Furthermore, the growth percentage in each well was calculated, when the number of living cells in the cell growth control was set to be 100%. The calculation results are shown in Tables 3 and 4. With regard to the cell death percentage and the cell growth percentage, the numerical value, to which the results obtained by the use of a single drug were added, was defined as an additive effect, and a case where cell growth inhibition and cell death percentage which exceeded the additive effect were obtained was defined as a synergistic effect. As shown in Table 3, synergistic cell growth inhibition effects were observed from a half or more of combined uses. Moreover, regarding the cell death percentage, synergistic cell death-enhancing effects were confirmed in all of the combined uses except for the lowest concentration of TfR436 and the lowest concentration of hydroxyurea (Table 4).

TABLE 3

Combined effects of PPMX-T003 and hydroxyurea
Cell growth inhibition percentage

| | PPMX-T003 (ng/mL) | | | | |
|---|---|---|---|---|---|
| HU (μM) | 0 | 37.5 | 75 | 150 | 300 |
| 0 | 0% (A) | 23% | 48% | 69% | 75% |
| 31.3 | 15% | (B) 54% | 89% | 93% | 94% |
| 62.5 | 28% | 83% | 95% | 96% | 96% |
| 125 | 52% | 94% | (C) 97% | 98% | 97% |
| 250 | 76% | 98% | 99% | 98% | 99% |

TABLE 4

Combined effects of PPMX-T003 and hydroxyurea
Cell death percentage

| | PPMX-T003 (ng/mL) | | | | |
|---|---|---|---|---|---|
| HU (μM) | 0 | 37.5 | 75 | 150 | 300 |
| 0 | 0% | 4% | 6% | 12% | 16% |
| 31.3 | 5% | 9% | 40% | 54% | 55% |
| 62.5 | (A) 7% | 27% | 65% | (B) 70% | 71% |
| 125 | 6% | 61% | 79% | 84% | 77% |
| 250 | 17% | 80% | 87% | 85% | 89% |

In the above tables, (A) indicates the percentage of cell growth inhibition or cell death by the use of a single drug, (B) indicates a combination (synergistic effect) which exceeds the additive effect (a total of inhibition percentages of single drugs, and (C) indicates a combination by which additive effects exceed 100%.

The invention claimed is:

1. A method of treating polycythemia in a subject in need thereof, comprising administering to the subject an antibody which recognizes the amino acids at positions 629 to 633 of a human transferrin receptor, wherein the antibody is an antibody having a heavy chain first complementarity determining region (VH CDR1), a heavy chain second complementarity determining region (VH CDR2), and a heavy chain third complementarity determining region (VH CDR3), of SEQ ID NOs: 1, 2, and 3, respectively, and also having a light chain first complementarity determining region (VL CDR1), a light chain second complementarity determining region (VL CDR2), and a light chain third complementarity determining region (VL CDR3), of SEQ ID NOs: 4, 5, and 6, respectively.

2. The method of claim 1, wherein the polycythemia is polycythemia vera.

3. The method of claim 1, wherein the antibody is administered in combination with another polycythemia treatment method.

4. The method of claim 1, wherein the antibody is an antibody having a heavy chain of SEQ ID NO: 7 and a light chain of SEQ ID NO: 8.

5. The method of claim 1, wherein the antibody is administered in combination with hydroxyurea.

6. The method of claim 2, wherein the antibody is an antibody having a heavy chain of SEQ ID NO: 7 and a light chain of SEQ ID NO: 8.

7. The method of claim 3, wherein the antibody is an antibody having a heavy chain of SEQ ID NO: 7 and a light chain of SEQ ID NO: 8.

8. The method of claim 2, wherein the antibody is a human antibody or a humanized antibody.

9. The method of claim 3, wherein the antibody is a human antibody or a humanized antibody.

10. The method of claim 1, wherein the antibody is a human antibody or a humanized antibody.

11. The method of claim 4, wherein the antibody is a human antibody or a humanized antibody.

* * * * *

SEQUENCE LISTING

<160> NUMBER OF SEQ ID NOS: 11

<210> SEQ ID NO 1
<211> LENGTH: 5
<212> TYPE: PRT
<213> ORGANISM: Homo sapiens

<400> SEQUENCE: 1

```
Ser Tyr Gly Met His
1               5
```

<210> SEQ ID NO 2
<211> LENGTH: 17
<212> TYPE: PRT
<213> ORGANISM: Homo sapiens

<400> SEQUENCE: 2

```
Val Ile Ser Tyr Asp Gly Ser Asn Lys Tyr Tyr Ala Asp Ser Val Lys
1               5                   10                  15

Gly
```

<210> SEQ ID NO 3
<211> LENGTH: 14
<212> TYPE: PRT
<213> ORGANISM: Homo sapiens

<400> SEQUENCE: 3

```
Asp Ser Asn Phe Trp Ser Gly Tyr Tyr Ser Pro Val Asp Val
1               5                   10
```

<210> SEQ ID NO 4
<211> LENGTH: 13
<212> TYPE: PRT
<213> ORGANISM: Homo sapiens

<400> SEQUENCE: 4

```
Thr Arg Ser Ser Gly Ser Ile Ala Ser Asn Ser Val Gln
1               5                   10
```

<210> SEQ ID NO 5
<211> LENGTH: 8
<212> TYPE: PRT
<213> ORGANISM: Homo sapiens

<400> SEQUENCE: 5

```
Tyr Glu Asp Thr Gln Arg Pro Ser
1               5
```

<210> SEQ ID NO 6
<211> LENGTH: 10
<212> TYPE: PRT
<213> ORGANISM: Homo sapiens

<400> SEQUENCE: 6

```
Gln Ser Tyr Asp Ser Ala Tyr His Trp Val
1               5                   10
```

<210> SEQ ID NO 7
<211> LENGTH: 123
<212> TYPE: PRT
<213> ORGANISM: Homo sapiens

<400> SEQUENCE: 7

```
Asp Val Gln Leu Val Gln Ser Gly Gly Gly Val Val Gln Pro Gly Arg
```

-continued

```
1               5                   10                  15

Ser Leu Arg Leu Ser Cys Ala Ala Ser Gly Phe Pro Phe Lys Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Arg Asp Ser Asn Phe Trp Ser Gly Tyr Tyr Ser Pro Val Asp Val
            100                 105                 110

Trp Gly Gln Gly Thr Thr Val Thr Val Ser Ser
        115                 120


<210> SEQ ID NO 8
<211> LENGTH: 111
<212> TYPE: PRT
<213> ORGANISM: Homo sapiens

<400> SEQUENCE: 8

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Ser Val Gln Trp Tyr Gln Gln Arg Pro Gly Ser Ala Pro Ile Thr Val
        35                  40                  45

Ile Tyr Glu Asp Thr Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Gln Thr Glu Asp Glu Ala Asp Tyr Tyr Cys Gln Ser Tyr Asp Ser
                85                  90                  95

Ala Tyr His Trp Val Phe Gly Gly Gly Thr Lys Leu Ala Val Leu
            100                 105                 110


<210> SEQ ID NO 9
<211> LENGTH: 760
<212> TYPE: PRT
<213> ORGANISM: Homo sapiens

<400> SEQUENCE: 9

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
```

-continued

```
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525
```

-continued

```
Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760


<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Recombinant
      tag

<400> SEQUENCE: 10

Ala Ala Ala Arg Gly Gly Pro Glu Gln Lys Leu Ile Ser Glu Glu Asp
1               5                   10                  15

Leu Asn Ser Ala Val Asp His His His His His His
            20                  25


<210> SEQ ID NO 11
<211> LENGTH: 15
<212> TYPE: PRT
<213> ORGANISM: Artificial Sequence
<220> FEATURE:
<223> OTHER INFORMATION: Synthetic

<400> SEQUENCE: 11

Gly Gly Gly Gly Ser Gly Gly Gly Gly Ser Gly Gly Gly Gly Ser
1               5                   10                  15
```